United States Patent
Bauer et al.

(10) Patent No.: US 6,533,738 B1
(45) Date of Patent: Mar. 18, 2003

(54) THERAPY APPARATUS FOR THE SHOCK WAVE TREATMENT OF A PATIENT

(75) Inventors: Edgar Bauer, Kraichtal (DE); Stefan Saelzler, Waghaeusel (DE)

(73) Assignee: Richard Wolf GmbH, Knittlingen (DE)

( * ) Notice: Subject to any disclaimer, the term of this patent is extended or adjusted under 35 U.S.C. 154(b) by 230 days.

(21) Appl. No.: 09/616,006

(22) Filed: Jul. 13, 2000

(30) Foreign Application Priority Data

Jul. 29, 1999 (DE) .......................................... 199 35 724

(51) Int. Cl.[7] .............................................. A61B 17/22
(52) U.S. Cl. ......................................................... 601/4
(58) Field of Search ........................... 601/2, 4; 600/439; 378/205

(56) References Cited

U.S. PATENT DOCUMENTS

| | | | |
|---|---|---|---|
| 4,194,510 A | | 3/1980 | Proudian |
| 4,237,901 A | | 12/1980 | Taenzer |
| 4,530,358 A | * | 7/1985 | Forssmann et al. ............. 601/4 |
| 4,977,888 A | * | 12/1990 | Rietter et al. .................. 601/4 |
| 5,060,634 A | * | 10/1991 | Belikan et al. ................. 601/4 |
| 5,113,848 A | | 5/1992 | Krauss et al. |
| 5,144,953 A | * | 9/1992 | Wurster et al. ............. 600/439 |
| 5,158,072 A | * | 10/1992 | Wess et al. ..................... 601/4 |
| 5,271,403 A | | 12/1993 | Paulos |
| 5,301,659 A | * | 4/1994 | Brisson et al. ................. 601/4 |
| 5,488,951 A | | 2/1996 | Bauer et al. |
| 6,231,530 B1 | * | 5/2001 | Haumann ..................... 601/4 |

FOREIGN PATENT DOCUMENTS

| | | |
|---|---|---|
| DE | 32 10 919 | 10/1983 |
| DE | 35 44 628 | 6/1987 |
| DE | 35 44 707 | 6/1987 |
| DE | 3926380 | 2/1991 |
| DE | 92 18 254.2 | 10/1993 |
| DE | 4404 140 | 10/1994 |
| DE | 196 30 180 | 7/1996 |
| DE | 195 09 004 | 10/1996 |
| DE | 197 18 511.8 | 4/1997 |
| DE | 43 00 740 | 3/1998 |
| DE | 197 33 233 | 9/1998 |
| EP | 0 106 292 | 4/1984 |
| EP | 0 265 741 | 5/1988 |
| EP | 42 35 34 | 4/1991 |
| EP | 0 443 379 | 8/1991 |
| EP | 1 072 226 A2 * | 1/2001 ............ A61B/17/22 |

* cited by examiner

Primary Examiner—Shawna J. Shaw
(74) Attorney, Agent, or Firm—Cohen, Pontani, Lieberman & Pavane

(57) ABSTRACT

Disclosed is an apparatus which comprises a main housing with a shock wave generator and with a coupling membrane and a receiving space arranged therebetween for a coupling fluid which can be controlled with respect to quantity. The receiving space communicates with a control space which can be impinged by a gaseous control force. For the supply of the gaseous control force to the control space a pressurized gas leading control conduit with only a slight flow cross section is required.

15 Claims, 5 Drawing Sheets

THERAPY APPARATUS FOR THE SHOCK WAVE TREATMENT OF A PATIENT

BACKGROUND OF THE INVENTION

The invention is in a therapy apparatus for the shock wave treatment of a patient.

A shock wave therapy apparatus is described in EP-A-0 265 741. It comprises at least one therapy head which comprises a shock wave generator, a coupling membrane on the patient side and arranged therebetween a receiving space for coupling fluid. To the receiving space there is connected a fluid circulation which apart from a circulatory pump comprises several valves and a bleeding means in order to keep the coupling fluid flowing through the receiving space in a controlled manner bubble-free also during the treatment. In order to ensure an adequate through-flow of the therapy head and to keep the coupling membrane always pressed tightly on the body of the patient to be treated, it is necessary for the coupling fluid to be circulated in the fluid circulation with an adequate pressure and in a sufficient quantity, for which the conduit cross sections of the circulation must be relatively large. This leads to the further disadvantage that the handling of the therapy head during the patient treatment is unwieldy and awkward on account of the relatively thick fluid conduits.

A further therapy apparatus is described in DE 197 18 511 A1. It comprises a therapy head essentially of the above mentioned type, which via an electronic conduit is connected to a supply and operation unit. The therapy head is a closed constructional unit and contains a coupling medium which cannot be changed in its quantity. In order to permit larger penetration depths of the therapy focus into the body of the patient, coupling attachments are allocated to the therapy head. Coupling attachments are loose parts and may be easily lost. Furthermore the field of application of this therapy head is limited by way of the external coupling attachments or coupling cushions, because the coupling membrane of the therapy head only permits a very small penetration depth of the therapy focus of the therapy head and because the external coupling cushions do not permit an infinitely adjustment of the therapy head. Furthermore the application of the therapy head is very awkward because the surgeon by way of the coupling cushion must gradually feel his way up to the location of therapy.

In DE 44 04 140 A1 there is described a further therapy apparatus. It serves the treatment of pain conditions and the influencing of vegetative nerve system and comprises a shock wave generator, a coupling membrane on the patient side, a receiving space with coupling fluid and a central locating device. The therapy head of the shock wave generator is located completely in the coupling fluid of the receiving space and therefore all around must be protected with respect to the coupling fluid, for which complicated sealings are required. Furthermore there is necessary a complicated adjusting mechanics in order to be able to adjust the therapy head to the region of therapy.

BRIEF SUMMARY OF THE INVENTION

The object of the invention lies in improving a therapy apparatus of the initially cited type as a hand apparatus, such that whilst maintaining an optimal execution of treatment of a patient, during this treatment one may operate simply and comfortably.

The therapy apparatus of the invention for the shock wave treatment of a patient has a main housing with a shock wave generator operable via a supply tubing with energy conduits and with a coupling membrane and a space with a coupling fluid. The quantity of the coupling fluid in the receiving space for the purpose of adjusting the coupling membrane to the patient is controllable. The receiving space containing the coupling fluid communicates with a control space which is likewise filled with coupling fluid and which at least partly comprises a flexible wall region, and wherein the flexible wall region of the control space can be impinged with a gaseous control force.

With the solution according to the invention the convenience of the therapy apparatus is significantly increased since the flow cross section of the control conduit for reducing and enlarging the coupling fluid quantity in the receiving space of the shock wave generator may now be kept very small since it is only necessary to lead a gas medium being under pressure, for example pressurized air, through this conduit which impinges the control space of the therapy apparatus with a gaseous pressure force. By way of the pressure force of the gas medium the flexible wall of the control space may be suitably pressed together or expanded so that the coupling fluid located in this space is pressed into the receiving space of the shock wave generator or may flow back again out of this, in order to be able to apply the coupling membrane of the shock wave generator on the body of a patient in a manner which is correct for the therapy. Thus no relatively sluggishly flowing fluid quantities need to be led through the control conduit of the common supply tubing, but only relatively quickly flowing pressure gases, by which means the concerned pressurized gas control conduit has a considerably smaller diameter than a corresponding fluid conduit, with the result that the supply tubing also containing electrical conduits for the shock wave generator, in its outer diameter may be kept considerably smaller than previously, which considerably increases the handiness of the therapy head whilst maintaining an exact and large-surface positionability of the coupling membrane of the shock wave generator on the patient.

In a preferred embodiment of the therapy apparatus according to the invention the control space is provided as a separate space in a rigid connection housing fastening on the outside to the main housing of the apparatus and that on this housing there is connectable a pressurized air conduit. The main housing is advantageously provided with an elongate handle in which the connection housing is contained and to which there is connectable a supply tubing which contains the pressurized air conduit for the control space, furthermore the handle is provided with an operating keyboard for the operation of the shock wave generator. By way of this the handiness of the therapy apparatus is considerably increased.

In a further preferred embodiment of the therapy head according to the invention there is provided a probing rod, with two end abutments and with a probing tip of X-ray opaque material, which is coaxially movable along an axis running through the focus of the shock wave generator and which from outside the main housing projects into the receiving space, wherein the front end abutment for the distal positioning of the probing tip is arranged in the focus of the shock wave generator. This permits a quick treatment positioning of the therapy apparatus at locations of treatment which are located in the region of the patient close to the skin.

In a further preferred embodiment the probing rod for purposes of bleeding may be designed at least partly as a hollow rod which in the region of its probing tip comprises at least one air inlet opening and in its section located outside the main housing at least one closable outlet opening.

The various features of novelty which characterize the invention are pointed out with particularity in the claims appended to and forming a part of this specification. For a better understanding of the invention, its operating advantages and specific objects obtained by its use, reference should be had to the accompanying drawings and descriptive matter in which there is illustrated and described a preferred embodiment of the invention.

DETAILED DESCRIPTION OF THE INVENTION

Figure 1:
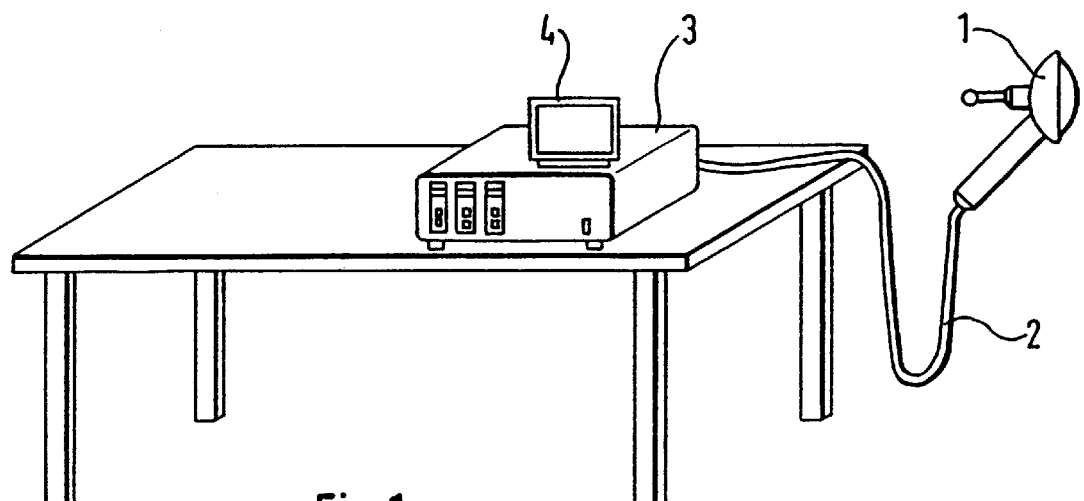
FIG. 1 shows a supply means to which a single embodiment example of a therapy apparatus is connected.

FIG. 1 shows a single therapy apparatus 1, for the shock wave treatment of a patient, which via a supply tubing 2 is connected to a supply means 3 with a monitor 4. The supply tubing 2 contains several supply conduits for the electrical and gaseous actuation of the apparatus 1 whose operation is controlled by the means 3 in a manner known per se. The means 3 is formed as a table apparatus, but may also be designed as a standing apparatus.

Figure 2:
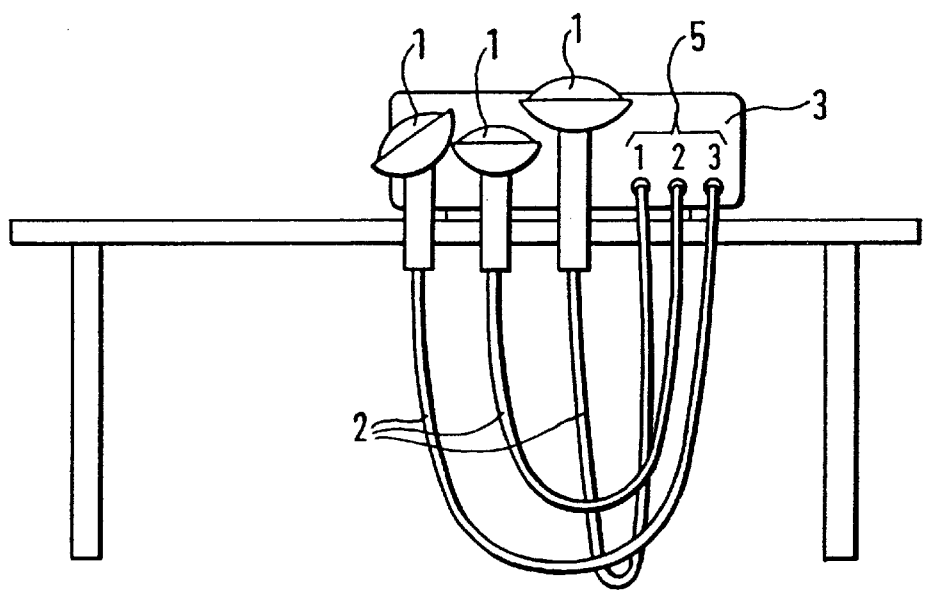
FIG. 2 shows a supply means, to which there are connected three units of the embodiment example.

FIG. 2 shows a supply means 3 with several therapy apparatus 1, for example with three therapy apparatus. This means has three plug locations 5 for the therapy apparatus in order for the desired treatment, in each case to be able to select the suitable therapy apparatus. Via a button of the means 3 the desired therapy apparatus is switched ready for operation. The several therapy apparatus according to FIG. 2 differ according to the required treatment purpose. Thus for example the size, aperture, penetration depth and the power of the therapy apparatus may be different. Furthermore the apparatus 1 may comprise a locating means or positioning aids of the known type. Further it is possible for the locating means and/or positioning aids to have differing frequencies for example in the case of ultrasound probes. Furthermore the therapy apparatus may have a coupling membrane adapted anatomically or to the corresponding symptoms, or a correspondingly adapted therapy head housing. Of course it is also possible that the supply tubings 2 may have a differing length.

Figure 3:
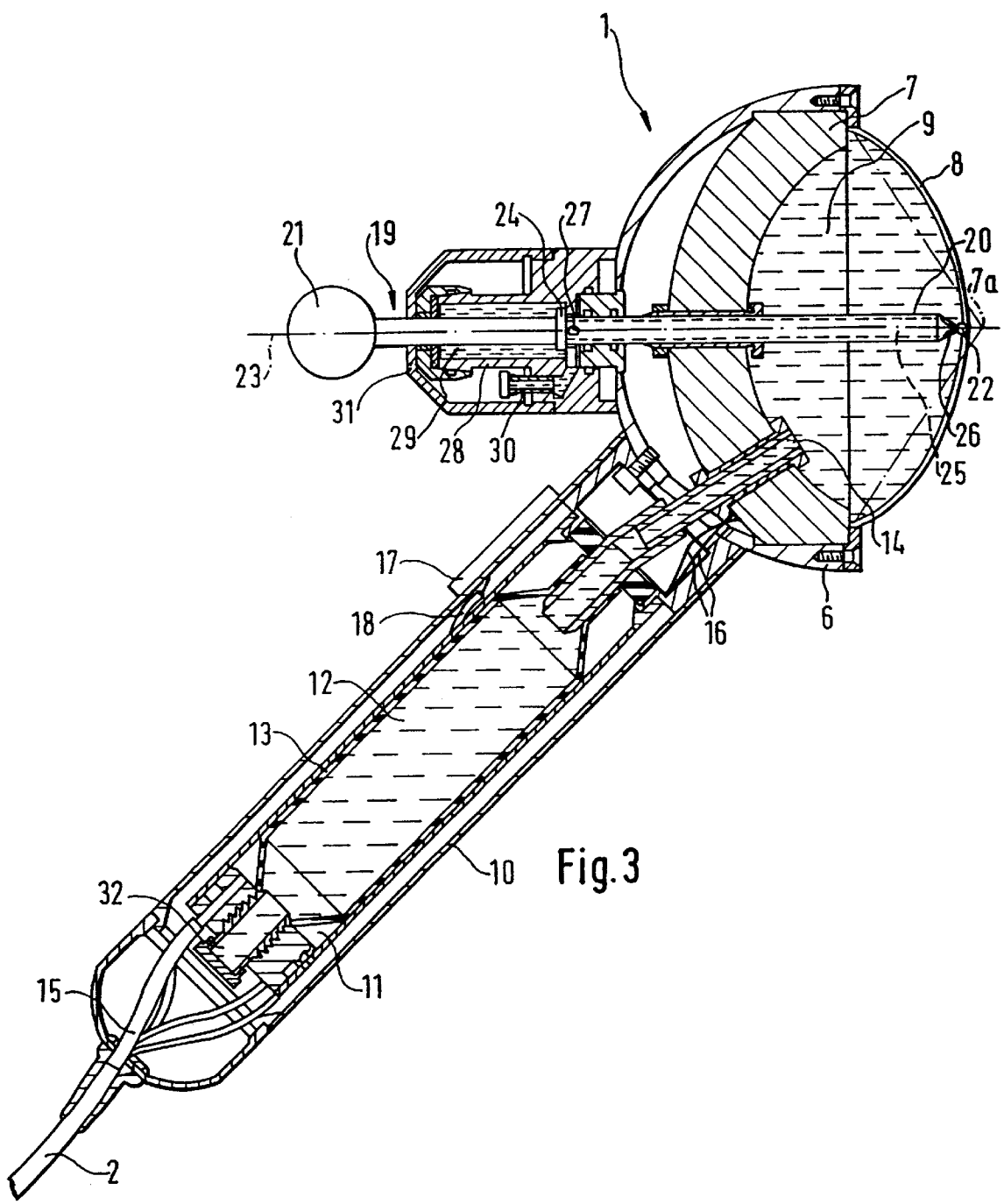
FIG. 3 shows the embodiment example in an axial section.

FIG. 3 the therapy apparatus 1 is shown in detail. In, for example, a calotte-shaped main housing 6, there is arranged a calotte-shaped shock wave generator 7. To the main housing there is fastened a calotte-shaped coupling membrane which occludes the shock wave generator to the outside in a closed-walled manner. Between the generator 7 and the coupling membrane 8 in the known manner there is formed a space 9 for receiving a coupling fluid. The quantity of the coupling fluid in the receiving space 9 is changeable depending on the respective therapy procedure, and is controlled by way of the supply means 3 via the supply tubing 2, as will yet be clear.

To the main housing 6 there is connected a rigid connection housing 10 which simultaneously may also be formed as an elongate, tubular handle with which the therapy apparatus during the treatment is held or can be fastened on a stand. It is possible, as FIG. 3 shows, in the connection housing 10 or in the handle to provide a further space 11 with rigid walls. This space or alternatively the connection housing contains a control space 12 which is formed at least partly flexible. The wall material of the control space 12 is a fluid-tight material, wherein this material may for example consist of rubber so that the control space, as shown in FIG. 3, is completely surrounded by a flexible wall 13. The thus flexible control space 12 is furthermore filled with coupling fluid.

Via a communicating passage 14 the flexible control space 12 is in flow connection with the receiving space 9 between the shock wave generator 7 and the coupling membrane 8.

To the other end of the connection housing 10 or of the handle there is connected the supply tubing 2 which leads to the mentioned supply means 3. In this supply means there runs a gaseous pressure conduit, for example a pressurized air conduit 15 in order to be able to impinge the flexible wall 13 of the flexible control space 12 in the rigid space 11 with pressurized air. In the condition ready for application the receiving space 9 and the control space 12 including the passage 14 are free of bubbles and completely filled with coupling fluid, wherein the coupling membrane does not necessarily have to have its outermost position.

If now the coupling membrane 8 is pressed against the treatment location of the patient or is applied thereon, then some coupling fluid flows out of the space 9 via the passage 14 back into the control space 12 whose flexible wall 13, or whose flexible wall region accordingly expands. Via the pressurized air conduit 15 then in a controlled manner pressurized air is introduced into the rigid space 11 and thus pressure is exerted onto the wall 13 of the control space 12. By way of this the volume of the control space 12 reduces by which means coupling fluid is pressed out of the control space 12 via the passage 14 again into the receiving space 9 in order to press the coupling membrane 8 onto the body of the patient in a large surfaced and tight manner. The pressurized air conduit 15 has in comparison to a previously used fluid conduit a considerably smaller flow cross section, through which however pressurized air may be led with the required rapidity in order to be able to carry out the corresponding volume change of the control space 12. By way of such a pressurized air conduit relatively small in cross section the supply tubing which also contains remaining conduits for the therapy apparatus 1, for example the electrical leads 16 for the shock wave generator 7, may be kept considerably smaller in cross section than previously, by which means the handiness of the therapy apparatus 1 is considerably improved.

For the further improved handling and operation of the therapy apparatus 1 the connection housing 10 or the handle may be provided with an operating keyboard 17 which via an electrical control conduit 18, which likewise runs through the supply tubing 2, is in connection with the supply means 3.

The therapy apparatus 1 may be provided with a positioning aid 19 for the correct application on the body of the patient. In the embodiment according to FIG. 3 this positioning aid consists of an axially movable probing rod 20 which is actuatable along any axis running through the therapy focus 7a of the shock wave generator 7. For this the probing rod has a proximal operating part 21 which is provided outside the main housing 6. The distal end of the probing rod 20 is formed as a probing tip 22 of X-ray opaque material, for example in the form of a metal ball. Preferably the probing rod 20 is axially movable along the central axis of symmetry 23 of the shock wave generator 7 and is provided with an abutment collar 24 in order at least to be able to determine the distal end position of the probing tip 22 of the probing rod 20 in the therapy focus 7a of the shock wave generator 7. The probing tip 22 may thus only be advanced so far until its position corresponds to that of the therapy focus of the shock wave generator. The symmetry axis 23 of the shock wave generator 7 is positioned exactly onto the treatment location, by which means the desired penetration depth may be defined. By way of this the treatment location on the patient may be probed with the bio-feedback treatment method.

In a further formation of the positioning aid 19 this may also be designed as a bleeding means on filling the receiving space 9 and the control space 12. For this the probing rod 20 is designed at least partly as a hollow rod, and specifically from the region of its probing tip 20 up to a location outside the main housing 6. Along this region there runs a bleeding channel 25 which in the region of the probing tip 22 comprises at least one air inlet opening 26 and at the location outside the main housing at least one air exit opening 27. This opening 27 may be directly closable.

The air exit opening 27 may however also be provided at the outer end of the probing rod 20, e.g. when the bleeding channel 25 extends through the whole probing rod up to its rear end on which then there is provided a closable connection piece.

Alternatively according to the illustrated embodiment it may be proceeded in that the probing rod 20 projecting to the rear out of the main housing 67 is surrounded by an auxiliary housing 28 connecting to the main housing, by which there is formed an annular space 29 which opens into an closable outlet connection piece 30 of the housing 28. If it is desired, the auxiliary housing 28 and the outlet connection piece 30 may be surrounded by a protective housing 31. The outlet opening 27 of the probing rod 30 thus opens into the annular space 29, and from here coupling fluid during the filling of the therapy apparatus 1 may flow downstream via the outlet connection piece 30. The probing rod 20 also in this case comprises a length such that it projects to the rear out of the housings 28 and 31 and may be actuated via the operating part 21.

For the filling of the receiving space 9 and of the control space 12 with coupling fluid the walling 13 of the control space is provided with an inlet connection piece 32. For filling these two spaces with coupling fluid the inlet connection piece 32 and the outlet connection piece 30 are connected to a filling circulation, for coupling fluid, which may comprise a bleeding means. For the bubble-free filling of the receiving section 9 the probing rod 20 is displaced forwards into its distal end position. Thus the coupling membrane 8 is pretensioned in a conical manner and via the inlet opening 26, of the probing rod 20, which is located in the frontmost region with a suitable posture of the therapy apparatus 1, the receiving space 9 is entirely bled of air and completely filled with coupling fluid. After a complete, bubble-free filling of the two spaces 9 and 12 the corresponding connection pieces 30 and 32 are again closed.

Figure 4:
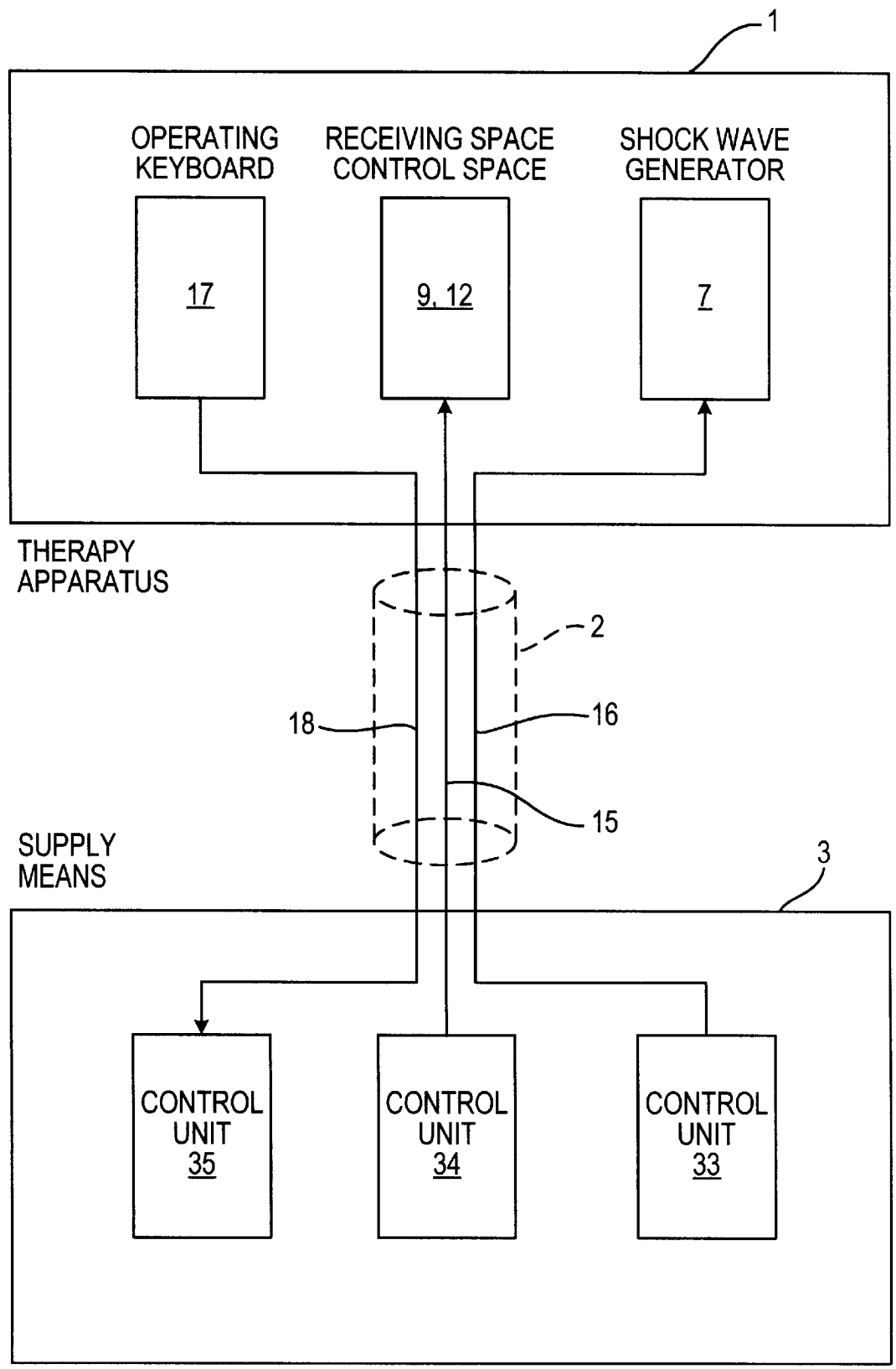
FIG. 4 shows a schematic circuit representation of an embodiment example connected to a supply means.

FIG. 4 shows a schematic circuit representation for the general control of the therapy apparatus 1. It will be understood that the shock wave generator 7, the spaces 9 and 12 for the coupling fluid and the operating keyboard 17 of the therapy apparatus 1 via the conduits 16, 15 and 18 running in the supply tubing 2 run to the supply means 3 where the corresponding control units 33, 34 and 35 for the corresponding parts of the therapy apparatus are provided.

Figure 5:
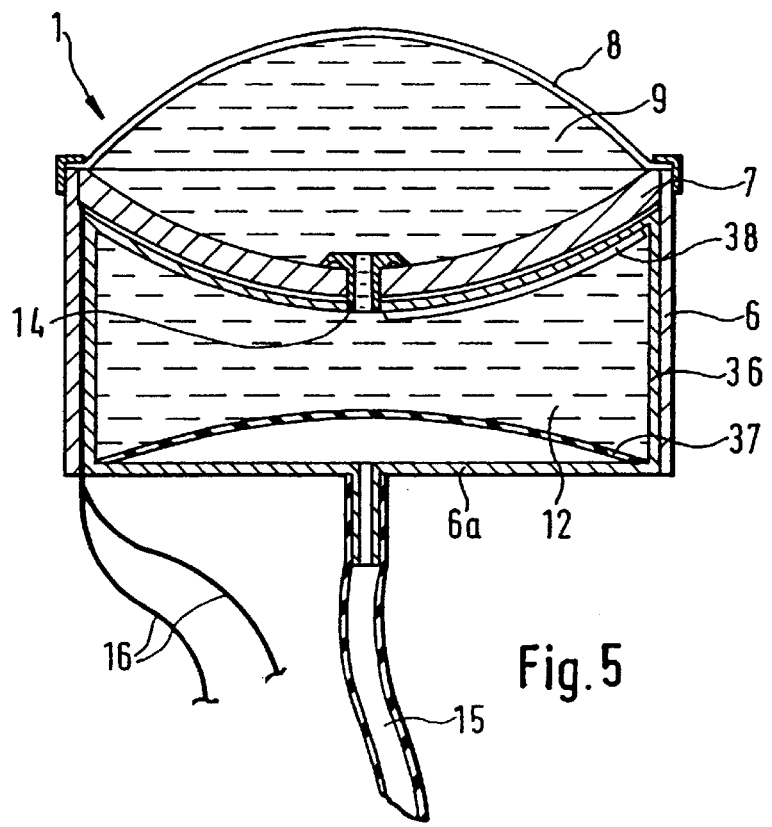
FIG. 5 shows a modified embodiment example, in an axial section.

FIG. 5 shows a modified embodiment example of the therapy apparatus 1. With this embodiment example a locating means or a positioning aid for determining the therapy region on the patient is not shown; known means for this may however be used internally or externally in combination with this embodiment example. Also with this embodiment example the receiving space 9 filled with coupling fluid is connected via the communicating passage 14 to a control space 12 located behind the shock wave generator 7. This control space is partly enclosed by a rigid wall 36 and partly by a flexible wall 37. With this there are provided components of the walls 36, 37 for forming the control space 12 within the main housing 6 of the therapy apparatus 1. The flexible wall part 37 in the initial condition projects somewhat with respect to the rear wall 6a of the main housing 6 as this is shown in FIG. 5. With a vacuum in the pressurized air conduit 15 the flexible wall part 37 is pulled in the direction of the rigid rear wall 6a with the result that coupling fluid escapes from the coupling space 9 via the passage 14 into the control space 12, so that the coupling membrane 8 is set back, thus moves in the direction of the shock wave generator 7. By way of this the therapy focus 7a reaches deeper locations in the patient to be treated. The flexible wall part 37 may be formed as a membrane of for example rubber material and extend over the whole cross sectional surface of the main housing 6, as shown, behind the shock wave generator. In an alternative formation of the flexible wall part a bellows-like balloon is provided at the pressurized air inflow region of the main housing 6.

In order to prevent, with the embodiment according to FIG. 5, the communication passage 14 between the two spaces 9 and 10 on the forwards movement and extension of the flexible wall part 37 from being closed, means 38 for holding free are provided in the region of the passage 14 provided here centrally in the shock wave generator. These means for holding free may consist of at least one tube piece which advantageously extends from the edge of the passage 14 roughly to the rigid wall part 36 of the control space 12. In the extreme case the flexible wall part 36 bears on the tube piece 38 so that the passage 14 is at least partly kept free.

The control leads 15 and 16 also in this example run through a supply tubing 2 which is small in cross section and which may connect directly to the rear wall 6a of the main housing 6 (not shown). They may initially also run through a handle (not shown) which connects to the rear wall 6a of the main housing 6 and then are led further in the tubing 2.

Figure 6:
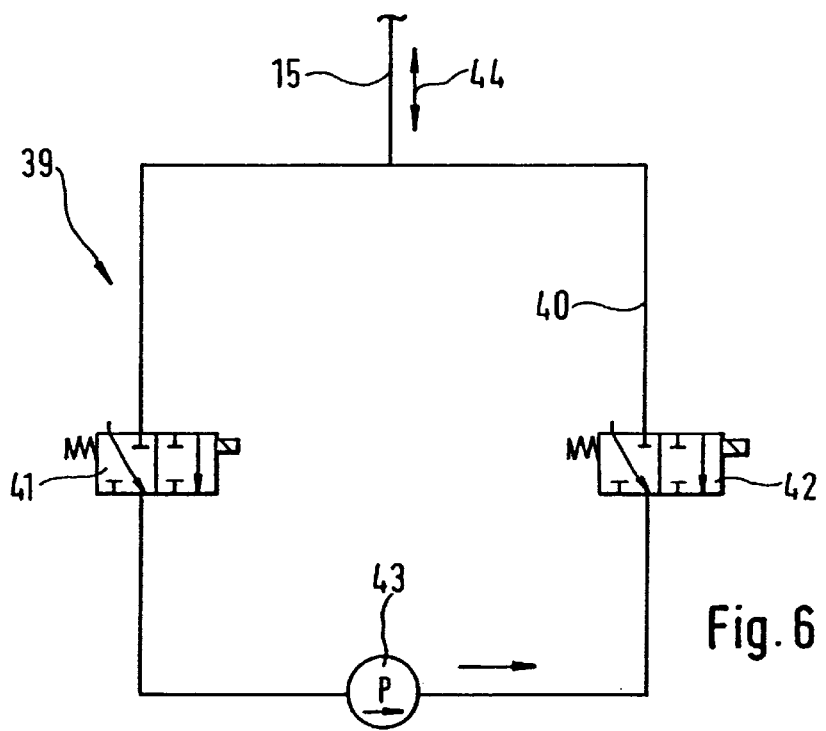
FIG. 6 shows a fluid control means for the embodiment example.

FIG. 6 shows a pneumatic control 39 for producing the control force in the pressurized air conduit 15 for the purpose of impinging the flexible wall parts 13 and 37 of the control space 12. In a conduit circuit 40 there are provided two control valves 41 and 42 as well as a circulatory pump 43 arranged between these two valves. According to the position of the control valves pressurized air according to the double arrow 44 is pumped through the conduit 15 in order to displace forwards or backwards the flexible wall part 13 or 37 of the control space 12. Via the passage 14 by way of this the corresponding quantity of coupling fluid in the receiving space 9 between the shock wave generator 7 and the coupling membrane 8 may be set according to the demand for the patient to be treated.

Figure 7:
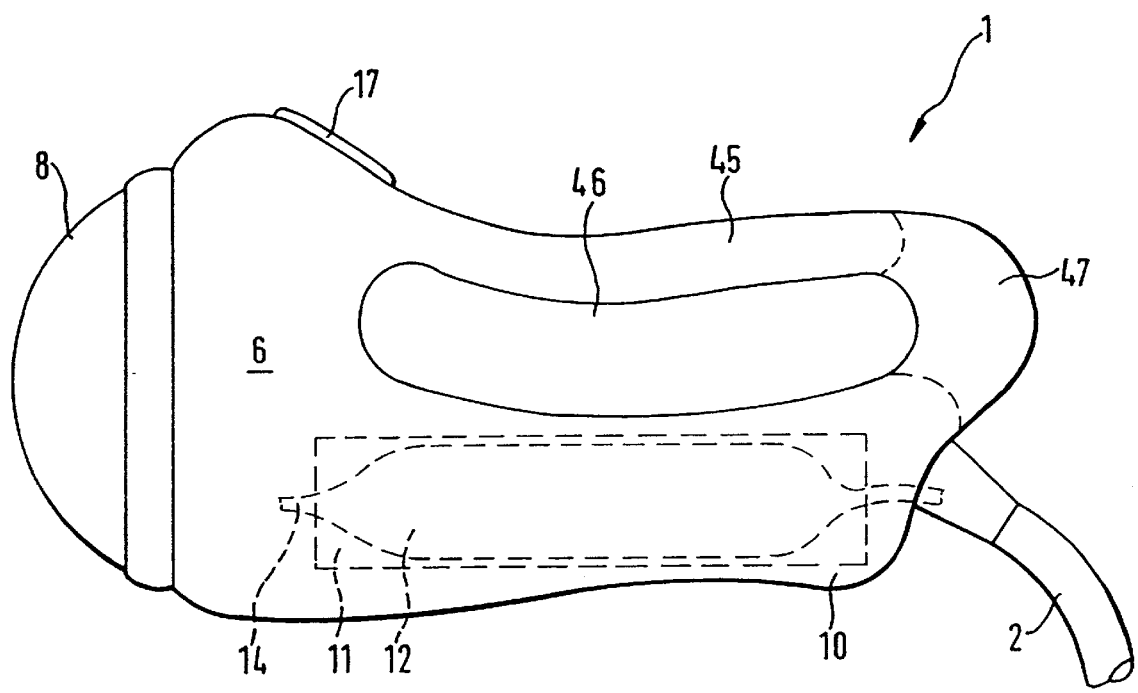
FIG. 7 shows a further modified embodiment example in a front view.

FIG. 7 shows a further modified embodiment of the invention. The main housing 6 of the therapy apparatus 1 is designed lengthened to the rear in a manner such that the lengthening comprises the connection housing 10, a web-like or elongate handle 45 and a grip slot 46 therebetween. In a modification the proximal, partly dashed shown region 47 of the apparatus 1 between the housing 10 and the handle 45 may also be done away with so that the grip slot 46 is open to the rear. In the connection housing 10 the space 11 with rigid walls, which is impinged with pressurized air from the supply tubing 2 and the flexible control space 12 therein is filled with the coupling fluid. The fingers of the surgeon grip through the grip slot 46 whilst he operates the keyboard 17 provided distally in the region of the grip 45 with the thumb. This construction of the therapy apparatus 1 has the advantage that the connection housing 10 and thus also the control space 12 located therein may be formed relatively large so that a relatively large quantity on controllable coupling fluid is made available, however that the apparatus 1 may be comfortably held and handled.

The terms and expressions which have been employed are used as terms of description and not of limitation, and there is no intention in the use of such terms and expressions of excluding any equivalent of the features shown and described or portions thereof, it being recognized that various modifications are possible within the scope of the invention.

What is claimed is:

1. A therapy apparatus for the shock wave treatment of a patient, comprising:
    a main housing with a handle, said handle having an operating keyboard for the operation of the therapy apparatus;
    a shock wave generator in said main housing, said generator operable via a supply tubing with energy conduits and with a coupling membrane:
    a receiving space with a coupling fluid between the generator and the membrane wherein the quantity of the coupling fluid in the receiving space for the purpose of adjusting the coupling membrane to the patient is controllable;
    a control space which communicates with the receiving space and which is filled with coupling fluid, said control space being at least partly bounded by a flexible wall region, and wherein a gaseous control force can impinge on the flexible wall region, wherein said control space is a separate space in a rigid connection housing fastened to the main housing and wherein a pressurized air conduit is connected to the connection housing and said handle forms, or contains, the connection housing.

2. The therapy apparatus of claim 1, wherein the shock wave generator has a therapy focus and said apparatus further comprises a probing rod which is axially movable along an axis running through the therapy focus of the shock wave generator and which projects into the receiving space, said probing rod having a probing tip of X-ray opaque material, as a positioning aid of the therapy apparatus.

3. The therapy apparatus of claim 2, wherein the probing tip is a metal ball.

4. The therapy apparatus of claim 2, wherein the probing tip has a distal end position and at least the distal end position of the probing tip of the probing rod is fixable by way of an abutment for the distal positioning of the probing tip in the therapy focus of the shock wave generator.

5. The therapy apparatus of claim 2, wherein the probing rod is at least partially formed as a hollow rod.

6. The therapy apparatus of claim 5, further comprising an auxiliary housing with an annular space wherein said auxiliary housing is connected to the main housing with a closable connection piece.

7. The therapy apparatus of claim 6, wherein the hollow probing rod axially protrudes through the auxiliary housing and wherein the at least one outlet opening of the probing rod opens into the annular space of the auxiliary housing.

8. The therapy apparatus of claim 5, wherein the least partially hollow rod has a section located outside the main housing and in the region of its probing tip comprises at least one inlet opening and in the section located outside the main housing comprises at least one exit opening.

9. The therapy apparatus of claim 1, wherein the main housing has an inner region behind the shock wave generator provided with a flexible wall, impingable with the gaseous control force, for forming and occluding the control space communicating with the receiving space for the coupling fluid in front of the shock wave generator.

10. The therapy apparatus of claim 9, wherein the main housing has a cross sectional surface and the flexible wall in the form of a membrane extends over the cross sectional surface behind the shock wave generator.

11. The therapy apparatus of claim 1, wherein the receiving space is in front of the shock wave generator and is connected to the control space behind the generator by way of a communicating passage for the coupling fluid.

12. The therapy apparatus of claim 11, wherein on the side of the control space, means for keeping free are allocated to the communicating passage.

13. The therapy apparatus of claim 12, wherein the means for keeping free comprises at least one tubular piece which serves the flexible wall as an abutment and whose one end borders the edge of the communicating passage.

14. The therapy apparatus of claim 1, further comprising a rear extension which has an elongate connection housing with the control space, an elongate handle and a grip slot therebetween.

15. The therapy apparatus of claim 1, wherein a supply tubing contains the pressurized air conduit for the supply of the control force for impinging the flexible wall region of the control space.

* * * * *